US010328008B2

(12) United States Patent
Yoshikawa et al.

(10) Patent No.: US 10,328,008 B2
(45) Date of Patent: *Jun. 25, 2019

(54) INTERNAL OLEFIN SULFONATE COMPOSITION

(71) Applicant: KAO CORPORATION, Tokyo (JP)

(72) Inventors: Yohei Yoshikawa, Wakayama (JP); Yoshinori Mitsuda, Wakayama (JP); Hiroshi Hori, Wakayama (JP); Yasuhiro Doi, Kainan (JP); Yoshifumi Nishimoto, Wakayama (JP)

(73) Assignee: KAO CORPORATION, Tokyo (JP)

( * ) Notice: Subject to any disclaimer, the term of this patent is extended or adjusted under 35 U.S.C. 154(b) by 40 days.

This patent is subject to a terminal disclaimer.

(21) Appl. No.: 15/674,373

(22) Filed: Aug. 10, 2017

(65) Prior Publication Data

US 2017/0340541 A1 Nov. 30, 2017

Related U.S. Application Data

(63) Continuation of application No. 14/764,304, filed as application No. PCT/JP2014/052257 on Jan. 31, 2014, now Pat. No. 9,789,045.

(30) Foreign Application Priority Data

Feb. 1, 2013 (JP) .................. 2013-018594

(51) Int. Cl.
| | | |
|---|---|---|
| C11D 1/00 | (2006.01) |
| A61K 8/46 | (2006.01) |
| A61Q 5/02 | (2006.01) |
| A61Q 19/10 | (2006.01) |
| C07C 309/20 | (2006.01) |
| A61K 8/04 | (2006.01) |
| C11D 1/37 | (2006.01) |
| C11D 3/00 | (2006.01) |
| C11D 1/29 | (2006.01) |
| C11D 1/14 | (2006.01) |

(52) U.S. Cl.
CPC ............ *A61K 8/466* (2013.01); *A61K 8/046* (2013.01); *A61Q 5/02* (2013.01); *A61Q 19/10* (2013.01); *C07C 309/20* (2013.01); *C11D 1/37* (2013.01); *C11D 3/0094* (2013.01); *C11D 1/143* (2013.01); *C11D 1/146* (2013.01); *C11D 1/29* (2013.01)

(58) Field of Classification Search
None
See application file for complete search history.

(56) References Cited

U.S. PATENT DOCUMENTS

| 3,332,878 A | 7/1967 | Coward |
| 3,781,339 A | 12/1973 | Tuvell et al. |
| 4,507,223 A | 3/1985 | Tano et al. |
| 4,555,351 A | 11/1985 | Morita et al. |
| 4,925,976 A | 5/1990 | Terao et al. |
| 5,078,916 A * | 1/1992 | Kok ........ C11D 1/143 510/488 |
| 2014/0079660 A1 | 3/2014 | Doi |
| 2014/0080751 A1 | 3/2014 | Yoshikawa et al. |

FOREIGN PATENT DOCUMENTS

| CA | 1338239 C | 4/1996 |
| CN | 1039803 A | 2/1990 |
| EP | 0351928 A1 | 1/1990 |
| EP | 0364012 A1 | 4/1990 |
| EP | 0377261 A2 | 7/1990 |
| EP | 0482687 A1 | 4/1992 |
| GB | 2 236 538 A | 4/1991 |
| JP | 58-157758 A | 9/1983 |
| JP | 59-27995 A | 2/1984 |
| JP | 59-222466 A | 12/1984 |
| JP | 60-32759 A | 2/1985 |
| JP | 61-134366 A | 6/1986 |
| JP | 2-90931 A | 3/1990 |
| JP | 3-126793 A | 5/1991 |
| JP | 3-126795 A | 5/1991 |
| JP | 2003-81935 A | 3/2003 |
| JP | 2014-76988 A | 5/2014 |
| JP | 2014-77126 A | 5/2014 |
| JP | 2015-27977 A | 2/2015 |
| JP | 2015-28123 A | 2/2015 |
| WO | WO 2010/129051 A1 | 11/2010 |
| WO | WO 2014/046175 A1 | 3/2014 |

(Continued)

OTHER PUBLICATIONS

International Search Report, issued in PCT/JP2014/052257, dated Apr. 8, 2014.
Extended European Search Report for European Application No. 14745566.1, dated Aug. 8, 2016.
International Preliminary Report on Patentability and an English translation of the Written Opinion of the International Searching Authority issued in the corresponding International Application No. PCT/JP2014/052257 dated Aug. 13, 2015.
Stapersma, et al., Hydroxy Alkane Sulfonate (HAS), a New Surfactant Based on Olefins, JAOCS, vol. 69, No. 1 (Jan. 1992).

*Primary Examiner* — Necholus Ogden, Jr.

(74) *Attorney, Agent, or Firm* — Birch, Stewart, Kolasch & Birch, LLP

(57) ABSTRACT

Provided are an internal olefin sulfonate composition which is capable of sufficiently enhancing foamability, foam dissipation property free from a slimy feeling during rinsing, and a feel after cleansing and subsequent drying, and a cleansing composition containing the same.

The internal olefin sulfonate composition comprises (A) an internal olefin sulfonate having 16 carbon atoms and (B) an internal olefin sulfonate having 12 carbon atoms, in which a content mass ratio of the component (A) to the component (B), (A/B), is from 10/90 to 90/10.

17 Claims, No Drawings

(56) References Cited

FOREIGN PATENT DOCUMENTS

WO    WO 2014/046176 A1    3/2014

\* cited by examiner

INTERNAL OLEFIN SULFONATE COMPOSITION

CROSS-REFERENCE TO RELATED APPLICATIONS

This application is a Continuation of U.S. patent application Ser. No. 14/764,304 filed on Jul. 29, 2015, which was filed as the National Phase of PCT International Application No. PCT/JP2014/052257 filed on Jan. 31, 2014, which claims the benefit of priority to Japanese Application No. 2013-018594 filed on Feb. 1, 2013, all of which are hereby expressly incorporated by reference into the present application.

FIELD OF THE INVENTION

The present invention relates to an internal olefin sulfonate composition useful as a base for a cleansing agent, and to a cleansing composition containing the internal olefin sulfonate composition.

BACKGROUND OF THE INVENTION

Anionic surfactant, particularly, alkyl sulfate and alkyl polyoxyalkylene sulfate, is excellent in detergency and foaming power, and thus are widely used as cleansing ingredients for domestic or industrial use. An olefin sulfonate, particularly, an internal olefin sulfonate obtained with an internal olefin having a double bond inside an olefin chain, not at its end, as a raw material, has been reported as one of the anionic surfactant.

Such an internal olefin sulfonate is generally obtained by sulfonating an internal olefin through reactions with a gaseous sulfur trioxide-containing gas, followed by neutralization and then hydrolysis of the resulting sulfonic acid. For example, Patent Document 1 discloses an improved production method thereof.

The internal olefin sulfonate thus obtained is known to have good biodegradability or the like, but is still insufficient in a basic performance as cleansing agent including foamability and foaming speed, compared with general-purpose surfactant such as alkyl polyoxyalkylene sulfuric acid ester salt. Thus, further improvement in such basic performance has been desired. As more people have concerned the water-saving or consumers' preferences have been diversified in recent years, the additional value of foam dissipation property free from a slimy feeling and a good feel after drying in addition to good foamability has also been required for use as major activator in laundry detergents, dishwashing detergents, shampoos or the like. Specifically, it has been desired to develop a surfactant composition having excellent foam dissipation property free from a slimy feeling during rinsing while bringing about a good feel without perceivable residue from the cleansing agent after cleansing and subsequent drying. Such an additional value is useful for, for example, body cleansers and hair shampoos. As more people have a habit to wash their hair or bodies within a limited time before leaving the house after awakening, or before going to bed, they are unsatisfied with a long time required for rinsing or an unpleasant feel after cleansing and subsequent drying. Particularly, young people, who have active metabolism and secrete a large amount of sebum, etc., tend to strongly desire a refreshed feel free from a slimy feeling on their scalps or bodies. If a surfactant composition which exerts foam dissipation property free from a slimy feeling and a good feel after drying can be formulated, this composition not only permits rinsing in a short time but can bring about a refreshed feel after drying, leading to the realization of water-saving.

Then, Patent Document 2 discloses a specific internal olefin sulfonic acid which is intended to impart the solubilizing ability, penetrating ability, and interfacial tension reducing ability as a cleansing component. It discloses that when it is used as, for example, a shampoo, it lathers well without friction, and achieves an improved feel. Patent Document 3 also describes a specific internal olefin sulfonate for the purposes of improving detergency, and discloses examples of application to shampoos, liquid soaps, and the like. Meanwhile, Patent Document 4 describes a promoter for recovering an oil using a surfactant containing a plurality of internal olefin sulfonates differing in the number of carbon atoms.

[Patent Document 1] JP-A-59-222466
[Patent Document 2] JP-A-2003-81935
[Patent Document 3] U.S. Pat. No. 5,078,916
[Patent Document 4] WO-A 2010/129051

SUMMARY OF THE INVENTION

The present invention relates to an internal olefin sulfonate composition comprising (A) an internal olefin sulfonate having 16 carbon atoms and (B) an internal olefin sulfonate having 12 carbon atoms, wherein a content mass ratio of the component (A) to the component (B), (A/B), is from 10/90 to 90/10.

The present invention also relates to a cleansing composition comprising (A) an internal olefin sulfonate having 16 carbon atoms and (B) an internal olefin sulfonate having 12 carbon atoms, wherein a content mass ratio of the component (A) to the component (B), (A/B), is from 10/90 to 90/10.

DETAILED DESCRIPTION OF THE INVENTION

Further improvement is still required for any of the compositions described in the above-mentioned documents to exert good foamability together with foam dissipation property free from a slimy feeling during rinsing and a feel after cleansing and subsequent drying at high levels as a cleansing agent which is applied to hair, the skin, or the like.

Therefore, the present invention relates to an internal olefin sulfonate composition which is capable of sufficiently enhancing foamability, foam dissipation property free from a slimy feeling during rinsing, and a feel after cleansing and subsequent drying, and a cleansing composition containing the internal olefin sulfonate composition.

The present inventors studied a length of an aliphatic chain in an internal olefin sulfonate, a ratio thereof and other various conditions, and consequently found that an internal olefin sulfonate composition which satisfies good foamability and can also exert excellent foam dissipation property free from a slimy feeling during rinsing while bringing about a good feel without perceivable residues from the cleansing agent after cleansing and subsequent drying can be obtained by setting the ratio between an internal olefin sulfonate having 16 carbon atoms and an internal olefin sulfonate having 12 carbon atoms to a predetermined range. On the basis of these findings, the present invention has been completed.

According to the present invention, it can provide an internal olefin sulfonate composition which satisfies good foamability and also exerts good foam dissipation property free from a slimy feeling during rinsing while sufficiently bringing about a good feel without perceivable residues from the cleansing agent after cleansing and subsequent towel drying, for example, and a cleansing composition containing the internal olefin sulfonate composition.

Hereinbelow, the present invention will be described in detail.

<Internal Olefin Sulfonate Composition>

The internal olefin sulfonate composition of the present invention includes (A) an internal olefin sulfonate having 16 carbon atoms and (B) an internal olefin sulfonate having 12 carbon atoms, in which a content mass ratio of the component (A) to the component (B), (A/B), is from 10/90 to 90/10.

In the present invention, an internal olefin sulfonate is a sulfonate obtained by sulfonating an internal olefin (an olefin having a double bond inside the olefin chain) as the raw material, followed by neutralization and then hydrolysis, as described above. That is, sulfonation of an internal olefin quantitatively produces β-sultone, some of which are converted into γ-sultone and olefin sulfonic acid, which are further converted into hydroxyalkane sulfonate and olefin sulfonate in the process of neutralization and hydrolysis (for example, J. Am. Oil Chem. Soc. 69, 39 (1992)). It should be noted that the above internal olefin may also has a broad meaning including a trace amount of so-called α-olefin, in which a double bond is present at the C-1 position of the carbon chain. Here, the hydroxyl group of the hydroxyalkane sulfonate thus obtained is present inside the alkane chain, and the double bond of the olefin sulfonate thus obtained is present inside the olefin chain. Also, the product thus obtained is mainly a mixture of the aforementioned substances, some of which may include a trace amount of hydroxyalkane sulfonate having a hydroxyl group at the end of the carbon chain, or olefin sulfonate having a double bond at the end of the carbon chain. In the present specification, each of these products and a mixture thereof are collectively referred to as internal olefin sulfonate. Hydroxyalkane sulfonate is referred to as the hydroxy form of an internal olefin sulfonate (hereinbelow, may also be referred to as HAS), and olefin sulfonate is referred to as the olefin form of an internal olefin sulfonate (hereinbelow, may also be referred to as IOS).

A content mass ratio of the component (A) to the component (B), (A/B), in the internal olefin sulfonate composition of the present invention is from 10/90 to 90/10 from the viewpoint of foamability, foaming speed, foam dissipation property free from a slimy feeling during rinsing, and a feel after cleansing and subsequent drying, and is preferably from 10/90 to 50/50, more preferably from 10/90 to 25/75, and even more preferably from 10/90 to 15/85, from the viewpoint of foam dissipation property free from a slimy feeling during rinsing and a feel after cleansing and subsequent drying. Also, the content mass ratio (A/B) is preferably from 25/75 to 75/25, more preferably from 40/60 to 75/25, and even more preferably from 40/60 to 60/40, from the viewpoint of foamability and foaming speed upon application to hair.

The content mass ratio of the component (A) to the component (B), (A/B), in the internal olefin sulfonate composition is a numerical value measured by a high-performance liquid chromatograph-mass spectrometer (hereinbelow, abbreviated as HPLC-MS). Specifically, an internal olefin sulfonate having 16 carbon atoms and an internal olefin sulfonate having 12 carbon atoms are separated by HPLC, each of which then is identified by analysis with MS. From the HPLC-MS peak area thereof, the content mass ratio of the component (A) to the component (B), (A/B), in the internal olefin sulfonate composition is obtained.

The total content of the component (A) and the component (B) in the internal olefin sulfonate composition of the present invention is preferably 50% by mass or more, more preferably 70% by mass or more, more preferably 80% by mass or more, more preferably 90% by mass or more, more preferably 95% by mass or more, more preferably 96.5% by mass or more, and even more preferably 97% by mass or more, from the viewpoint of foamability, foaming speed, foam dissipation property free from a slimy feeling during rinsing, and a feel after cleansing and subsequent drying. The upper limit of the total content of the component (A) and the component (B) is preferably 100% by mass.

As is apparent from the aforementioned production method, the sulfonate group in the internal olefin sulfonate of the present invention is present inside the olefin chain or alkane chain. In the present invention, it is preferable that the content of an internal olefin sulfonate in which the sulfonate group is present at the C-2 position of the olefin chain or alkane chain is low, while the content of an internal olefin sulfonate in which the sulfonate group is present further inside is high, from the viewpoint of foamability, foaming speed, foam dissipation property free from a slimy feeling during rinsing, and a feel after cleansing and subsequent drying. It is more preferable that the content of an internal olefin sulfonate in which the sulfonate group is present at the C-2 position of the olefin chain or alkane chain is low, with respect to both of the above internal olefin sulfonates having 16 carbon atoms and 12 carbon atoms.

The content of the internal olefin sulfonate in which a sulfonate group is present at a C-2 position in the internal olefin sulfonate (component (A) and component (B)) having 16 and 12 carbon atoms of the present invention is, in the total content of the component (A) and the component (B), preferably 25% by mass or less, more preferably 22% by mass or less, more preferably less than 20% by mass, and even more preferably less than 18% by mass, from the viewpoint of foamability, foaming speed, foam dissipation property free from a slimy feeling during rinsing, and a feel after cleansing and subsequent drying. The content of the internal olefin sulfonate in which a sulfonate group is present at a C-2 position in the component (A) and the component (B) is, in the total content of the component (A) and the component (B), preferably 5% by mass or more, more preferably 7% by mass or more, and even more preferably 10% by mass or more, from the viewpoint of foamability, foaming speed, foam dissipation property free from a slimy feeling during rinsing, and a feel after cleansing and subsequent drying, cost, and productivity. Considering these viewpoints together, the content of the internal olefin sulfonate in which a sulfonate group is present at a C-2 position in the component (A) and the component (B) is, in the total content of the component (A) and the component (B), preferably 5% by mass or more and 25% by mass or less, more preferably 7% by mass or more and 22% by mass or less, more preferably 7% by mass or more and less than 20% by mass, more preferably 7% by mass or more and less than 18% by mass, and even more preferably 10% by mass or more and less than 18% by mass.

The content of the internal olefin sulfonate in which a sulfonate group is present at a C-2 position in the component (A) and the component (B) is, in the total content of the component (A) and the component (B), preferably 22% by mass or less and more preferably less than 20% by mass, and preferably 12% by mass or more, more preferably 14% by mass or more, more preferably 17% by mass or more, and even more preferably 19% by mass or more, from the viewpoint of foam dissipation property free from a slimy feeling during rinsing and a feel after cleansing and subsequent drying. Also, the content of the internal olefin sulfonate in which a sulfonate group is present at a C-2 position in the component (A) and the component (B) is, in the total content of the component (A) and the component (B), preferably 12% by mass or more and 22% by mass or less, more preferably 14% by mass or more and 22% by mass or less, more preferably 17% by mass or more and less than 20% by mass, and even more preferably 19% by mass or more and less than 20% by mass, from a similar viewpoint.

The content of the internal olefin sulfonate in which a sulfonate group is present at a C-2 position in the component (A) and the component (B) is, in the total content of the component (A) and the component (B), preferably less than 20% by mass, more preferably 19% by mass or less, and even more preferably 17% by mass or less, and preferably 12% by mass or more and more preferably 14% by mass or more, from the viewpoint of foamability and foaming speed during hair cleansing. Also, the content of the internal olefin sulfonate in which a sulfonate group is present at a C-2 position in the component (A) and the component (B) is, in the total content of the component (A) and the component (B), preferably 12% by mass or more and less than 22% by mass, more preferably 14% by mass or more and 19% by mass or less, and even more preferably 14% by mass or more and 17% by mass or less, from a similar viewpoint.

The content of the internal olefin sulfonate in which a sulfonate group is present at a C-2 position in the component (A) and the component (B) is, in the total content of the component (A) and the component (B), preferably 22% by mass or less and more preferably 19% by mass or less, and preferably 12% by mass or more, more preferably 14% by mass or more, and even more preferably 17% by mass or more, from the viewpoint of foaming speed during skin cleansing. Also, the content of the internal olefin sulfonate in which a sulfonate group is present at a C-2 position in the component (A) and the component (B) is, in the total content of the component (A) and the component (B), preferably 12% by mass or more and 22% by mass or less, more preferably 14% by mass or more and 19% by mass or less, and even more preferably 17% by mass or more and 19% by mass or less, from a similar viewpoint.

A content of the α-olefin sulfonate in which the sulfonate group is positioned at the C-1 position of an olefin chain or an alkane chain is, in the total content of the component (A) and the component (B), preferably less than 2.8% by mass and more preferably 2.0% by mass or less, from the viewpoint of foam dissipation property free from a slimy feeling during rinsing and a feel after cleansing and subsequent drying. The content of the α-olefin sulfonate in which the sulfonate group is positioned at the C-1 position of an olefin chain or an alkane chain is, in the total content of the component (A) and the component (B), preferably 0.01% by mass or more, more preferably 0.1% by mass or more, and even more preferably 0.3% by mass or more, from the viewpoint of cost and productivity. Considering these viewpoints together, the content of the α-olefin sulfonate in which the sulfonate group is positioned at the C-1 position of an olefin chain or an alkane chain is, in the total content of the component (A) and the component (B), preferably 0.01% by mass or more and less than 2.8% by mass, more preferably 0.1% by mass or more and less than 2.8% by mass, more preferably 0.3% by mass or more and less than 2.8% by mass, and even more preferably 0.3% by mass or more and 2.0% by mass or less.

It should be noted that the content of the internal olefin sulfonate in which the sulfonate group is present at the C-2 position in the internal olefin sulfonate having 16 and 12 carbon atoms may be measured by a method such as nuclear magnetic resonance spectroscopy. More specifically, it is a numerical value measured by a method using gas chromatography described later in Example.

A content mass ratio of the hydroxy form to the olefin form, (hydroxy form/olefin form), in the internal olefin sulfonate having 16 and 12 carbon atoms is preferably from 50/50 to 100/0, more preferably from 60/40 to 100/0, more preferably from 70/30 to 100/0, more preferably from 75/25 to 100/0, and even more preferably from 75/25 to 95/5, from the viewpoint of foam dissipation property free from a slimy feeling during rinsing and a feel after cleansing and subsequent drying.

The content mass ratio of the hydroxy form and the olefin form in the internal olefin sulfonate having 16 and 12 carbon atoms of the present invention may be measured by the method described later in Examples.

A content of an internal olefin sulfonate having 18 or more carbon atoms in the internal olefin sulfonate composition of the present invention is preferably 5% by mass or less, more preferably 3% by mass or less, more preferably 2% by mass or less, and even more preferably 1% by mass or less, from the viewpoint of foam dissipation property free from a slimy feeling during rinsing and a feel after cleansing and subsequent drying. The lower limit of the content of the internal olefin sulfonate having 18 or more carbon atoms is preferably 0% by mass, that is, it is preferable that the internal olefin sulfonate composition of the present invention does not contain the internal olefin sulfonate having 18 or more carbon atoms unless this internal olefin sulfonate is inevitably mixed therein.

Also, for the internal olefin sulfonate having 18 or more carbon atoms, it is also preferable to have a low content of the internal olefin sulfonate in which the sulfonate group is positioned at the C-2 position of an olefin chain or an alkane chain and a high content of the internal olefin sulfonate in which the sulfonate group is positioned more internally, from the viewpoint of foam dissipation property free from a slimy feeling during rinsing and a feel after cleansing and subsequent drying.

As the internal olefin sulfonate composition of the present invention is obtained by sulfonating an internal olefin, followed by neutralization and hydrolysis as described above, an unreacted raw material internal olefin and inorganic compounds may remain in the composition. It is preferred that the contents of these components are much smaller.

A content of the raw material internal olefin in the internal olefin sulfonate composition of the present invention is preferably less than 5.0% by mass, more preferably less than 3.0% by mass, more preferably less than 1.5% by mass, more preferably less than 1.0% by mass and even more preferably less than 0.05% by mass with respect to the amount of the internal olefin sulfonate from the viewpoint of foam dissipation property free from a slimy feeling during rinsing and a feel after cleansing and subsequent drying.

The content of the unreacted internal olefin may be measured by a method described later in Examples.

A content of the inorganic compounds in the internal olefin sulfonate composition of the present invention is preferably less than 7.5% by mass, more preferably less than 5.0% by mass, more preferably less than 3.0% by mass, and even more preferably less than 1.0% by mass with respect to the amount of the internal olefin sulfonate from the viewpoint of foam dissipation property free from a slimy feeling during rinsing and a feel after cleansing and subsequent drying.

In this context, the inorganic compound includes sulfate and alkali agent. The content of these inorganic compounds may be measured by a potentiometric titration. Specifically, the content may be measured by a method described later in Examples.

The internal olefin sulfonate composition of the present invention may contain a hydroxy form and an olefin form having any number of carbon atoms which are different from that of the component (A) and the component (B). The number of carbon atoms in the hydroxy form and the olefin form other than the component (A) and the component (B) is preferably from 8 to 24, more preferably from 14 to 20, more preferably 14 or 18, and even more preferably 14 from the viewpoint of foam dissipation property free from a slimy feeling during rinsing and a feel after cleansing and subsequent drying. These hydroxy forms and olefin forms having various numbers of carbon atoms are derived from the internal olefin used as a raw material.

The internal olefin sulfonate composition of the present invention may contain other components, for example, water as a medium, a pH adjuster, a viscosity reducing agent, an organic solvent, and polyhydric alcohols, in addition to the components described above.

<Method for Producing Internal Olefin Sulfonate Composition>

The internal olefin sulfonate composition may be produced by sulfonating a raw material internal olefin composition containing a raw material internal olefin having 8 to 24 carbon atoms, followed by neutralization and hydrolysis. More specifically, for example, the composition may be produced in accordance with the methods described in U.S. Pat. Nos. 1,633,184 and 2,625,150, and Tenside Surf. Det. 31 (5) 299 (1994), and the like.

As mentioned above, in the present invention, a raw material internal olefin refers to an olefin substantially having a double bond inside the olefin chain. A content of the α-olefin in which a double bond is present at a C-1 position in the raw material internal olefin is, in the total content of the component (A) and the component (B), preferably less than 2.8% by mass and more preferably 2.0% by mass or less, from the viewpoint of foam dissipation property free from a slimy feeling during rinsing and a feel after cleansing and subsequent drying. The content of the α-olefin in which a double bond is present at a C-1 position in the raw material internal olefin is, in the total content of the component (A) and the component (B), preferably 0.01% by mass or more, more preferably 0.1% by mass or more, and even more preferably 0.3% by mass or more, from the viewpoint of cost and productivity. Considering these viewpoints together, the content of the α-olefin sulfonate in which the sulfonate group is positioned at the C-1 position of an olefin chain or an alkane chain is, in the total content of the component (A) and the component (B), preferably 0.01% by mass or more and less than 2.8% by mass, more preferably 0.1% by mass or more and less than 2.8% by mass, more preferably 0.3% by mass or more and less than 2.8% by mass, and even more preferably 0.3% by mass or more and 2.0% by mass or less.

From the viewpoint of foam dissipation property free from a slimy feeling during rinsing and a feel after cleansing and subsequent drying of the internal olefin sulfonate composition obtained thus, the number of carbon atoms in the raw material internal olefin is preferably from 8 to 24, more preferably from 12 to 20, more preferably from 12 to 18, more preferably from 12 to 16, and even more preferably 12 and 16. An internal olefin to be used as a raw material may be used singly, or a combination of two or more thereof may be used.

When the internal olefin sulfonate composition is obtained by sulfonating the raw material internal olefin composition, followed by neutralization and hydrolysis, the content of the internal olefin in which a double bond is present at a C-2 position in the raw material internal olefin composition is preferably from 15 to 45% by mass, more preferably from 15 to 40% by mass, and even more preferably from 15 to 35% by mass.

In the synthesis of the internal olefin sulfonate composition, the content of the raw material internal olefin in which a double bond is present at a C-2 position in the raw material internal olefin composition may be measured by a gas chromatograph (hereinbelow, abbreviated as GC). Specifically, this content may be measured by the method described later in Examples.

The raw material internal olefin composition may contain a paraffin component. A content of the paraffin component is preferably less than 5% by mass, more preferably less than 3% by mass, more preferably 1% by mass or less, and even more preferably 0.1% by mass or less, from the viewpoint of foam dissipation property free from a slimy feeling during rinsing and a feel after cleansing and subsequent drying.

The content of the paraffin component may be measured by, for example, GC-MS.

The sulfonation reaction may be carried out by reacting a sulfur trioxide gas with a raw material internal olefin composition at a ratio of from 1 to 1.2 moles of sulfur trioxide per mole of the raw material internal olefin. The reactions may be carried out at a reaction temperature of from 20 to 40° C.

Neutralization is carried out by reacting from 1 to 1.5 times the molar amount of an alkaline aqueous solution such as sodium hydroxide, potassium hydroxide, ammonia or 2-aminoethanol with the theoretical value of sulfonate group.

The hydrolysis reaction may be carried out at from 90 to 200° C. for from 30 minutes to three hours in the presence of water. These reactions may be successively carried out. Also, upon completion of the reactions, the products may be purified by extraction, washing, or the like.

Also, in the production of the internal olefin sulfonate composition, the raw material internal olefin in which the number of carbon atoms is distributed in from 8 to 24 may be subjected as a raw material internal olefin composition to sulfonation, neutralization, and hydrolysis to produce the internal olefin sulfonate composition. Alternatively, the raw material internal olefin having a uniform number of carbon atoms may be subjected to sulfonation, neutralization, and hydrolysis to produce internal olefin sulfonic acid, which is then mixed with a plurality of internal olefin sulfonates each having different number of carbon atoms to produce the internal olefin sulfonate composition.

The internal olefin sulfonate composition of the present invention exerts good foamability together with foam dissipation property free from a slimy feeling during rinsing and a feel after cleansing and subsequent drying at high levels, and is thus useful as a cleansing ingredient. Specifically, it can be used in household cleansing agents such as hair shampoos, body cleansers, laundry detergents, and kitchen detergents, and is particularly useful as a base for the hair shampoo.

<Cleansing Composition>

The cleansing composition of the present invention is not particularly limited as long as it contains (A) an internal olefin sulfonate having 16 carbon atoms and (B) an internal olefin sulfonate having 12 carbon atoms, wherein a content mass ratio of the component (A) to the component (B), (A/B), is from 10/90 to 90/10, as in the internal olefin sulfonate composition of the present invention. The cleansing composition of the present invention may contain other components depending on the intended purpose. Examples of the other components include other surfactant, a foaming increasing agent, and an auxiliary agent or the like. The total content of (A) the internal olefin sulfonate having 16 carbon atoms and (B) the internal olefin sulfonate having 14 carbon atoms in the cleansing composition is preferably from 0.1 to 80% by mass, more preferably from 1 to 50% by mass, and even more preferably from 2 to 30% by mass.

The other surfactant is preferably, for example, an alkyl sulfate or an alkyl polyoxyalkylene sulfate. Examples of the auxiliary agent include, but not particularly limited to, water, polymer, an oil solution, silicone, a moisturizing agent, a viscosity regulator, a preservative, an anti-inflammatory agent, an antioxidant, an ultraviolet absorber, a sequestering agent, a pearlescent agent, a dye, a fragrance, an enzyme, a bleaching agent, a bleach activator, and a pH adjuster.

The cleansing composition of the present invention may be produced, for example, by formulating the internal olefin sulfonate composition obtained as described above, and may be produced by further mixing the internal olefin sulfonate composition with the components described above.

In relation to the embodiments mentioned above, the present invention further discloses the following internal olefin sulfonate composition and cleansing composition:

<1> An internal olefin sulfonate composition comprising (A) an internal olefin sulfonate having 16 carbon atoms and (B) an internal olefin sulfonate having 12 carbon atoms, wherein a content mass ratio of the component (A) to the component (B), (A/B), is from 10/90 to 90/10.

<2> The internal olefin sulfonate composition according to <1>, wherein the content mass ratio of the component (A) to the component (B), (A/B), in the internal olefin sulfonate composition is preferably from 10/90 to 50/50, more preferably from 10/90 to 25/75, and even more preferably from 10/90 to 15/85.

<3> The internal olefin sulfonate composition according to <1>, wherein the content mass ratio of the component (A) to the component (B), (A/B), in the internal olefin sulfonate composition is preferably from 25/75 to 75/25, more preferably from 40/60 to 75/25, and even more preferably from 40/60 to 60/40.

<4> The internal olefin sulfonate composition according to any one of <1> to <3>, wherein a total content of the component (A) and the component (B) in the internal olefin sulfonate composition is preferably 50% by mass or more, more preferably 70% by mass or more, more preferably 80% by mass or more, more preferably 90% by mass or more, more preferably 95% by mass or more, more preferably 96.5% by mass or more, and even more preferably 97% by mass or more, with its upper limit being preferably 100% by mass.

<5> The internal olefin sulfonate composition according to any one of <1> to <4>, wherein a content of the internal olefin sulfonate in which a sulfonate group is present at a C-2 position in the internal olefin sulfonate having 16 and 12 carbon atoms is preferably 25% by mass or less and more preferably 22% by mass or less, and preferably 5% by mass or more and more preferably 7% by mass or more.

<6> The internal olefin sulfonate composition according to any one of <1> to <5>, wherein a mass ratio of a content of a hydroxy form to a content of an olefin form, (hydroxy form/olefin form), in the internal olefin sulfonate having 16 and 12 carbon atoms is preferably from 50/50 to 100/0, more preferably from 60/40 to 100/0, more preferably from 70/30 to 100/0, more preferably from 75/25 to 100/0, and even more preferably from 75/25 to 95/5.

<7> The internal olefin sulfonate composition according to any one of <1> to <6>, wherein a content of a raw material internal olefin in the internal olefin sulfonate composition is preferably less than 5.0% by mass, more preferably less than 3.0% by mass, more preferably less than 1.5% by mass, more preferably less than 1.0% by mass, and even more preferably less than 0.05% by mass with respect to the amount of the internal olefin sulfonate.

<8> The internal olefin sulfonate composition according to any one of <1> to <7>, wherein a content of inorganic compound in the internal olefin sulfonate composition is preferably less than 7.5% by mass, more preferably less than 5.0% by mass, more preferably less than 3.0% by mass, and even more preferably less than 1.0% by mass with respect to the amount of the internal olefin sulfonate.

<9> The internal olefin sulfonate composition according to any one of <1> to <8>, wherein the number of carbon atom in the hydroxy form and the olefin form other than component (A) and component (B) in the internal olefin sulfonate composition is preferably from 8 to 24, more preferably from 14 to 20, more preferably 14 or 18, and even more preferably 14.

<10> The internal olefin sulfonate composition according to any one of <1> to <9>, obtained by sulfonating a raw material internal olefin composition containing an internal olefin, followed by neutralization and then hydrolysis, with a content of the internal olefin in which a double bond is present at a C-2 position being preferably from 15 to 45% by mass.

<11> The internal olefin sulfonate composition according to <10>, wherein a content of the internal olefin in which a double bond is present at a C-2 position in the raw material internal olefin composition is from 15 to 40% by mass.

<12> A cleansing composition obtained by formulating the internal olefin sulfonate composition according to any one of <1> to <11>.

<13> A cleansing composition comprising (A) an internal olefin sulfonate having 16 carbon atoms and (B) an internal olefin sulfonate having 12 carbon atoms, wherein a content mass ratio of the component (A) to the component (B), (A/B), is from 10/90 to 90/10.

<14> The cleansing composition according to <12> or <13>, wherein a content of the internal olefin sulfonate is preferably from 0.1 to 80% by mass.

<15> The cleansing composition according to any one of <12> to <14>, further comprising one or more preferably selected from the group consisting of an alkyl sulfate and an alkyl polyoxyalkylene sulfate.

<16> A method for washing hair, comprising applying the cleansing composition according to any one of <12> to <15> to hair, followed by washing and then rinsing.

<17> A method for washing skin, comprising applying the cleansing composition according to any one of <12> to <15> to skin, followed by rinsing.

<18> Use of the cleansing composition according to any one of <12> to <15> for washing hair.

<19> Use of the cleansing composition according to any one of <12> to <15> for washing skin.

EXAMPLES

Hereinbelow, the present invention will be specifically described with reference to Examples. It should be noted that unless otherwise specifically noted, the content of each of the components is expressed by % by mass in the following Tables. Also, the methods for measuring various physical properties are as follows.

(1) Conditions of Measurement (i) Method for Measuring the Position of a Double Bond in the Internal Olefin The position of a double bond in an internal olefin was measured by gas chromatography (hereinbelow, abbreviated as GC). Specifically, an internal olefin was converted to a dithiated derivative by reaction with dimethyl disulfide, and then each component was separated by GC. The position of a double bond in an internal olefin was determined by the peak area of each component.

The apparatus and analytical conditions used for the measurement are as follows. GC apparatus "HP6890" (the product of Hewlett-Packard Company); Column "Ultra-Alloy-1HT capillary column" (30 m×250 μm×0.15 μm, the product of Frontier Laboratories Ltd.); Detector (hydrogen flame ionization detector (FID)); Injection temperature of 300° C.; Detector temperature of 350° C.; and He flow rate of 4.6 mL/min.

(ii) Method for Measuring the Content of Internal Olefin Sulfonate in which a Sulfonate Group is Present at a C-2 Position The linkage position of the sulfonate group was measured by GC. Specifically, the internal olefin sulfonate was reacted with trimethylsilyldiazomethane to form a methyl-esterified derivative. Then, each component was separated by GC. Each of a peak area was regarded as a mass ratio, and the content of internal olefin sulfonate in which a sulfonate group is present at a C-2 position was quantitated.

The apparatus and analytical conditions used for the measurement are as follows. GC apparatus "Agilent technology 6850" (the product of Agilent Technologies, Inc.); Column "HP-1 capillary column" (30 m×320 μm×0.25 μm, the product of Agilent Technologies, Inc.); Detector (hydrogen flame ionization detector (FID)); Injection temperature of 300° C.; Detector temperature of 300° C.; He flow rate of 1.0 mL/min.; and Oven (60° C. (0 min.)→10° C./min.→300° C. (10 min.)).

(iii) Method for Measuring the Mass Ratio of Hydroxy Form/Olefin Form

The mass ratio of hydroxy form/olefin form was measured by HPLC-MS. Specifically, the hydroxy form and the olefin form were separated by HPLC and each form was identified by separately analyzing with MS. From the resulting GC-MS peak area, the fraction of each form was determined.

The apparatus and analytical conditions used for the measurement are as follows. HPLC apparatus "Agilent technology 1100" (the product of Agilent Technologies, Inc.); Column "L-column ODS 4.6×150 mm" (the product of Chemicals Evaluation and Research Institute, Japan); Sample preparation (diluted 1000-fold with methanol); Eluent A (10 mM ammonium acetate in water); Eluent B (10 mM ammonium acetate in methanol), Gradient (0 min (A/B=30/70%)→10 min (30/70%)→55 min (0/100%)→65 min (0/100%)→66 min (30/70%)→75 min (30/70%)); MS apparatus "Agilent technology 1100 MS SL (G1946D)" (the product of Agilent Technologies, Inc.); and MS detection (anion detection m/z 60-1600, UV 240 nm).

(iv) Method for Measuring the Content of the Raw Material Internal Olefin

The content of the raw material internal olefin was measured by GC. Specifically, ethanol and petroleum ether were added to an aqueous solution of internal olefin sulfonate, followed by extraction to give olefin in the petroleum ether phase. From the GC peak area of the olefin, the amount thereof was quantitated.

The apparatus and analytical conditions used for the measurement are as follows. GC apparatus "Agilent technology 6850" (the product of Agilent Technologies, Inc.); Column "Ultra-Alloy-1HT capillary column, 15 m×250 μm×0.15 μm" (the product of Frontier Laboratories, Ltd.); Detector (hydrogen flame ionization detector (FID)); Injection temperature of 300° C.; Detector temperature of 350° C.; and He flow rate of 3.8 mL/min.

(v) Method for Measuring the Content of Inorganic Compound

The content of inorganic compound was measured by potentiometric titration and neutralization titration. Specifically, the content of $Na_2SO_4$ was quantitated by measuring sulfate ion ($SO_4^{2-}$) by potentiometric titration. Also, the content of NaOH was quantitated by neutralization titration with diluted hydrochloric acid.

(vi) Method for Measuring the Content of the Paraffin Component

The content of the paraffin component was measured by GC. Specifically, ethanol and petroleum ether were added to an aqueous solution of internal olefin sulfonate, followed by extraction to give paraffin in the petroleum ether phase. From the GC peak area of the paraffin, the amount thereof was quantitated.

It should be noted that the apparatus and analytical conditions used are the same as those used for the measurement of the content of the raw material internal olefin.

(2) Production of an Internal Olefin

[Production Example A] Synthesis of C16 Internal Olefins in which 16.3% by Mass of Double Bonds was Present at C-2 Position Into a flask with a stirrer, 7000 g (28.9 moles) of 1-hexadecanol "KALCOL 6098" (the product of Kao Corporation), and as a solid acid catalyst, 700 g (10% by mass relative to the raw material alcohol) of γ-alumina (STREM Chemicals, Inc.) were placed, and a reaction was allowed to proceed for five hours at 280° C. while stirring and passing nitrogen (7000 mL/minute) through the system. The alcohol conversion ratio was 100% and the purity of C16 internal olefin was 99.7% after the completion of the reaction. The resulting crude internal olefin was transferred to a distillation flask and distilled at from 136 to 160° C./4.0 mmHg, whereby 100% pure internal olefin having 16 carbon atoms was obtained. The double bond distribution in the resulting internal olefin was 0.7% by mass at C-1 position, 16.3% by mass at C-2 position, 15.1% by mass at C-3 position, 15.7% by mass at C-4 position, 17.1% by mass at C-5 position, 14.2% by mass at C-6 position, and 20.8% by mass at sum of C-7 and 8 positions.

[Production Example B] Synthesis of C12 Internal Olefins in which 33.1% by Mass of Double Bonds was Present at C-2 Position Into a flask with a stirrer, 6000 g (26.7 moles) of 1-dodecene "LINEALENE 12" (manufactured by Idemitsu Kosan Co., Ltd.), and as a solid acid catalyst, 180 g (3% by mass relative to the raw material α-olefin) of protic β-zeolite "CP-814E, Zeolyst International, Inc." were placed, and the reaction was allowed to proceed for 20 hours at 120° C. while stirring. Subsequently, the crude internal olefin was transferred to a distillation flask and distilled at from 124 to 136° C./7.5 mmHg, whereby 100% pure internal olefin having 12 carbon atoms was obtained. The double bond distribution in the resulting internal olefin was 0.5% by mass at C-1 position, 33.1% by mass at C-2 position, 23.7% by mass at C-3 position, 21.2% by mass at C-4 position, 15.0% by mass at C-5 position, and 6.6% by mass at C-6 position.

(3) Production of an Internal Olefin Sulfonate

Production Example 1 (Synthesis of C16 Internal Olefin Sulfonate)

Into a thin film sulfonation reactor having an outer jacket, the internal olefin having 16 carbon atoms (the content of an internal olefin in which a double bond is present at a C-2 position is 16.3% by mass) obtained in Production Example A was placed, and the sulfonation reaction was carried out by using sulfur trioxide gas under conditions of passing cooling water at 20° C. through the outer jacket of the reactor. The molar ratio of $SO_3$/internal olefin for the sulfonation reaction was set at 1.09. The resulting sulfonation product was added to an alkaline aqueous solution prepared with 1.5 times the molar amount of sodium hydroxide relative to the theoretical acid value, followed by neutralization at 30° C. for one hour while stirring. The resulting neutralized product was hydrolyzed by heating at 160° C. for one hour in an autoclave, whereby a crude product of sodium C16 internal olefin sulfonate was obtained. Then, 300 g of the crude product was transferred to a separatory funnel, to which 300 mL of ethanol was added and then 300 mL of petroleum ether was added per operation, whereby oil-soluble impurities were removed by extraction. At this time, inorganic compounds (mainly composed of sodium sulfate) which were precipitated at the oil-water interface by the addition of ethanol were also separated and removed from the aqueous phase by the oil-water separation operation. The above removal/extraction operation was repeated three times. Then, the aqueous phase side was evaporated to dryness, whereby sodium C16 internal olefin sulfonate was obtained. The mass ratio of hydroxy foam (sodium hydroxyalkane sulfonate)/olefin form (sodium olefin sulfonate) in the obtained sodium internal olefin sulfonate was 88/12. Also, the content of the raw material internal olefin contained in the obtained sodium internal olefin sulfonate was less than 100 ppm (below the GC detection limit), and that of inorganic compounds was 0% by mass. Also, the content of an internal olefin sulfonate in which a sulfonate group is present at a C-2 position was 9.3% by mass.

Production Example 2 (Synthesis of C12 Internal Olefin Sulfonate)

A sodium C12 internal olefin sulfonate was obtained under the same conditions as those used in Production Example 1 from the internal olefin having 12 carbon atoms (the content of an internal olefin in which a double bond is present at a C-2 position is 33.1% by mass) obtained in Production Example B.

The mass ratio of hydroxy form/olefin form in the obtained sodium internal olefin sulfonate was 92/8. Also, the content of the raw material internal olefin contained in the obtained sodium internal olefin sulfonate was less than 100 ppm (below the GC detection limit) and that of inorganic compounds was 0.2% by mass. Also, the content of an internal olefin sulfonate in which a sulfonate group is present at a C-2 position was 21.0% by mass.

Production Example 3

The composition obtained in Production Example 1 and the composition obtained in Production Example 2 were formulated and mixed at a mass ratio of 10:90 to obtain internal olefin sulfonate composition 1.

Production Example 4

The composition obtained in Production Example 1 and the composition obtained in Production Example 2 were formulated and mixed at a mass ratio of 25:75 to obtain internal olefin sulfonate composition 2.

Production Example 5

The composition obtained in Production Example 1 and the composition obtained in Production Example 2 were formulated and mixed at a mass ratio of 50:50 to obtain internal olefin sulfonate composition 3.

Production Example 6

The composition obtained in Production Example 1 and the composition obtained in Production Example 2 were formulated and mixed at a mass ratio of 75:25 to obtain internal olefin sulfonate composition 4.

Production Example 7

The composition obtained in Production Example 1 and the composition obtained in Production Example 2 were formulated and mixed at a mass ratio of 90:10 to obtain internal olefin sulfonate composition 5.

<Hair Evaluation>

A hair bundle (hair of a Japanese person free from treatment such as bleach or hair color; approximately 20 cm, 15 g) was cleansed with a plain shampoo shown in Table 1. Then, after application of a plain rinse shown in Table 2, the hair bundle was rinsed off with tap water to obtain a tress for evaluation.

Each of the internal olefin sulfonate compositions 1 to 5 obtained in Production Examples 3 to 7 was dissolved in ion-exchange water to prepare an aqueous solution (13% by mass) of the internal olefin sulfonate composition. Using these aqueous solutions, five expert panelists evaluated their foamability, foaming speed, foam dissipation property (free from a slimy feeling during rinsing), and feel after cleansing and subsequent towel drying in accordance with evaluation criteria and evaluation methods shown below. Specifically, 1.0 g of each cleansing composition shown in Table 3 was applied to the tress for evaluation and subjected to lathering, cleansing, and then rinsing. The results are shown in Table 3.

Table 3 also shows the evaluation results with reference to alkyl polyoxyethylene sulfate (AES), α-olefin sulfonate (AOS), and secondary alkyl sulfonate (SAS). The concentrations of these surfactants in the cleansing compositions were adjusted to 13% by mass.

TABLE 1

| (Composition of plain shampoo) | |
|---|---|
| (Component) | (%) |
| Sodium polyoxyethylene lauryl ether sulfate (42.0% in terms of EMAL E-27C (manufactured by Kao Corp.; 27% by weight of active component)) | 11.3 |
| Coconut oil fatty acid N-methylethanolamide (AMINON C-11S (manufactured by Kao Corp.)) | 3.0 |

TABLE 1-continued (Composition of plain shampoo)

| (Component) | (%) |
|---|---|
| Citric acid | 0.2 |
| Methylparaben | 0.3 |
| Purified water | Balance |
| Total | 100.0 |

(Production of Plain Shampoo)

The components were placed in a beaker, heated to 80° C., and then mixed. After confirmation of uniform dissolution, the mixture was cooled to obtain a plain shampoo.

TABLE 2

(Composition of plain rinse)

| (Component) | (%) |
|---|---|
| Octadecyloxypropyl trimethyl ammonium chloride (6.7% in terms of QUARTAMIN E-80K (manufactured by Kao Corp.; 45% by weight of active component)) | 3.0 |
| Stearyl alcohol (KALCOL 8098 (manufactured by Kao Corp.)) | 6.0 |
| Methylparaben | 0.3 |
| Purified water | Balance |
| Total | 100.0 |

(Production of Plain Rinse)

Octadecyloxypropyl trimethyl ammonium chloride and stearyl alcohol were placed in a beaker (A) and melted by heating to 80° C. Purified water and methylparaben were placed in another beaker (B) and heated to 80° C. while stirring. After confirmation of uniform dissolution, the mixed solution in the beaker (A) was added to the beaker (B) while stirring at 80° C., and an emulsification was carried out for 30 minutes. The heating was terminated, and it was cooled to room temperature to obtain a plain rinse.

<Evaluation Criteria and Evaluation Methods>

Foamability

5: Foaming properties were very good

4: Foaming properties were good

3: Ordinary foamability (equivalent to Reference Comparative Example 3: SAS)

2: Foaming properties were poor

1: Foaming properties were too poor to cleanse hair

Foaming Speed

5: Lathering was very quick and facilitated cleansing

4: Lathering was quick

3: Ordinary (equivalent to Reference Comparative Example 2: AOS)

2: Lathering was slow

1: Lathering was very slow

Foam Dissipation Property (Free from a Slimy Feeling During Rinsing)

5: Foam was very quickly dissipated and easily rinsed without a slimy feeling

4: Foam was quickly dissipated and sliminess was hardly felt

3: Ordinary (equivalent to Reference Comparative Example 2: AOS)

2: Foam was slowly dissipated and sliminess was felt

1: Foam was very slowly dissipated and hardly rinsed with persistent sliminess

Feel after Cleansing and Subsequent Towel Drying

5: Cleansing finish was very refreshing without perceivable residues from the cleansing agent 4: Cleansing finish was slightly refreshing 3: Ordinary (equivalent to Reference Comparative Example 1: AES)

2: Cleansing finish was hardly refreshing with slightly perceivable residues from the cleansing agent 1: Cleansing finish was not refreshing with strongly perceivable residues from the cleansing agent <Hand Wash Evaluation>

Each of the internal olefin sulfonate compositions 1 to 5 obtained in Production Examples 3 to 7 was dissolved in ion-exchange water to prepare an aqueous solution (13% by mass) of the internal olefin sulfonate composition. Using these aqueous solutions, five panelists washed their hands, and evaluated foamability, foaming speed, foam dissipation property (free from a slimy feeling during rinsing), and feel after cleansing and subsequent towel drying in accordance with the following evaluation criteria and evaluation method. Specifically, 1.0 g of aqueous solution (13% by mass) prepared by using the internal olefin sulfonate compositions shown in Table 3 was applied to the hands and subjected to lathering, cleansing, and then rinsing. The results are shown in Table 3.

<Evaluation Criteria>

Foaming Speed

5: Lathering was very quick and facilitated cleansing

4: Lathering was quick

3: Ordinary (equivalent to Reference Comparative Example 2: AOS)

2: Lathering was slow

1: Lathering was very slow

Foam Dissipation Property (Free from a Slimy Feeling During Rinsing)

5: Foam was very quickly dissipated and easily rinsed without a slimy feeling

4: Foam was quickly dissipated and sliminess was hardly felt

3: Ordinary (equivalent to Reference Comparative Example 1: AES)

2: Foam was slowly dissipated and sliminess was felt

1: Foam was very slowly dissipated and hardly rinsed with persistent sliminess

Feel after Cleansing and Subsequent Towel Drying

5: Cleansing finish was very refreshing without perceivable residues from the cleansing agent 4: Cleansing finish was slightly refreshing 3: Ordinary (equivalent to Reference Comparative Example 2: AOS)

2: Cleansing finish was hardly refreshing with slightly perceivable residues from the cleansing agent 1: Cleansing finish was not refreshing with strongly perceivable residues from the cleansing agent

TABLE 3

|  |  | Internal olefin sulfonate composition | | | | | Reference Comparative Examples | | |
|---|---|---|---|---|---|---|---|---|---|
|  |  | 1 | 2 | 3 | 4 | 5 | 1 | 2 | 3 |
| Internal olefin sulfonate composition | The number of carbon atoms in internal olefin sulfonate (mass ratio within parentheses) | 16/12 (10/90) | 16/12 (25/75) | 16/12 (50/50) | 16/12 (75/25) | 16/12 (90/10) | AES *1 | AOS *2 | SAS *3 |
|  | Total content of C16/12 (%) | 100 | 100 | 100 | 100 | 100 |  |  |  |
|  | Hydroxy form/olefin form | 92/8 | 91/9 | 90/10 | 89/11 | 88/12 |  |  |  |
|  | Amount of raw material internal olefin relative to amount of C16/12 internal olefin sulfonate | <100 ppm | <100 ppm | <100 ppm | <100 ppm | <100 ppm |  |  |  |
|  | Ratio of sulfonate group present at C-2 position in C16/12 internal olefin sulfonate (%) | 19.8 | 18.1 | 15.2 | 12.2 | 10.5 |  |  |  |
|  | Ratio of double bond present at C-2 position in raw material internal olefin (%) | 31.4 | 28.9 | 24.7 | 20.5 | 18.0 |  |  |  |
|  | Amount of inorganic compound (%) | 0.2 | 0.2 | 0.1 | 0.1 | 0.0 |  |  |  |
| Evaluation results | Hair evaluation — Foamability | 3.8 | 4.2 | 4.6 | 4.4 | 4.2 | 2.0 | 2.4 | 3.0 |
|  | Foaming speed | 4.0 | 4.0 | 4.6 | 4.0 | 3.4 | 2.0 | 3.0 | 3.4 |
|  | Foam dissipation property during rinsing | 5.0 | 4.8 | 4.4 | 3.8 | 3.6 | 2.6 | 3.0 | 1.6 |
|  | Feel after cleansing and subsequent towel drying | 4.8 | 4.2 | 3.8 | 3.4 | 3.2 | 3.0 | 3.4 | 2.4 |
|  | Hand wash evaluation — Foaming speed | 4.6 | 4.8 | 4.4 | 4.0 | 3.8 | 2.0 | 3.0 | 3.4 |
|  | Foam dissipation property during rinsing | 5.0 | 4.6 | 4.2 | 4.2 | 4.0 | 3.0 | 3.2 | 2.0 |
|  | Feel after cleansing and subsequent towel drying | 5.0 | 4.8 | 4.6 | 4.4 | 4.2 | 2.6 | 3.0 | 1.8 |

*1: Sodium alkyl polyoxyethylene sulfate (AES), manufactured by Kao Corp., EMAL 270S (active component: 70%)
*2: Sodium α-olefin sulfonate (AOS), manufactured by Lion Corp., LIPOLAN LB-440 (active component: 36%)
*3: Secondary sodium alkyl sulfonate (SAS), manufactured by LANXESS K.K., Mersolat H95 (active component: 95%)

INDUSTRIAL APPLICABILITY

The internal olefin sulfonate composition of the present invention can exert good foamability together with foam dissipation property free from a slimy feeling during rinsing and a feel after cleansing and subsequent drying at high levels. Thus, the internal olefin sulfonate composition of the present invention can be used suitably in the fields of household cleansing agents such as hair shampoos, body cleansers, laundry detergents, kitchen detergents, and residential detergents, and is also suitable for cosmetic emulsifiers, industrial emulsifiers, industrial cleansing agents or the like.

The invention claimed is:

1. An internal olefin sulfonate composition comprising (A) an internal olefin sulfonate having 16 carbon atoms and (B) an internal olefin sulfonate having 12 carbon atoms, wherein a content mass ratio of the component (A) to the component (B), (A/B), is from 10/90 to 90/10, and wherein a content of the internal olefin sulfonate in which a sulfonate group is present at a C-2 position in the internal olefin sulfonate having 16 and 12 carbon atoms is 25% by mass or less.

2. The internal olefin sulfonate composition according to claim 1, wherein a total content of (A) the internal olefin sulfonate having 16 carbon atoms and (B) the internal olefin sulfonate having 12 carbon atoms in the internal olefin sulfonate composition is from 50 to 100% by mass.

3. The internal olefin sulfonate composition according to claim 1, wherein a mass ratio of a content of a hydroxy form in the internal olefin sulfonate having 16 and 12 carbon atoms to a content of an olefin form in the internal olefin sulfonate having 16 and 12 carbon atoms, (hydroxy form/olefin form), is from 50/50 to 100/0.

4. The internal olefin sulfonate composition according to claim 1, wherein a content of a raw material internal olefin in the internal olefin sulfonate composition is less than 5.0% by mass with respect to the amount of the internal olefin sulfonate.

5. The internal olefin sulfonate composition according to claim 1, wherein a content of an inorganic compound in the internal olefin sulfonate composition is less than 7.5% by mass with respect to the amount of the internal olefin sulfonate.

6. The internal olefin sulfonate composition according to claim 1, obtained by sulfonating a raw material internal olefin composition containing a raw material internal olefin, followed by neutralization and then hydrolysis, with a content of the raw material internal olefin in which a double bond is present at a C-2 position being from 15 to 45% by mass.

7. The internal olefin sulfonate composition according to claim 1, wherein a content of the raw material internal olefin in which a double bond is present at a C-2 position in the raw material internal olefin composition is from 15 to 35% by mass.

8. The internal olefin sulfonate composition according to claim 1, wherein a content mass ratio of the component (A) to the component (B), (A/B), in the internal olefin sulfonate composition is from 10/90 to 15/85.

9. The internal olefin sulfonate composition according to claim 1, wherein a content mass ratio of the component (A) to the component (B), (A/B), in the internal olefin sulfonate composition is from 40/60 to 60/40.

10. A cleansing composition obtained by formulating the internal olefin sulfonate composition according to claim 1.

11. A cleansing composition comprising (A) an internal olefin sulfonate having 16 carbon atoms and (B) an internal olefin sulfonate having 12 carbon atoms, wherein a content mass ratio of the component (A) to the component (B), (A/B), is from 10/90 to 90/10.

12. The cleansing composition according to claim 11, wherein a total content of (A) the internal olefin sulfonate having 16 carbon atoms and (B) the internal olefin sulfonate having 12 carbon atoms is from 0.1 to 80% by mass.

13. The cleansing composition according to claim 11, comprising one or more selected from the group consisting of an alkyl sulfate and an alkyl polyoxyalkylene sulfate.

14. The cleansing composition according to claim 11 for dishwashing.

15. The cleansing composition according to claim 11 for laundry detergent.

16. The cleansing composition according to claim 11 for washing hair.

17. The cleansing composition according to claim 11 for washing skin.

\* \* \* \* \*